United States Patent
Lunte et al.

(10) Patent No.: US 10,121,645 B2
(45) Date of Patent: Nov. 6, 2018

(54) SHEATHLESS INTERFACE FOR CAPILLARY ELECTROPHORESIS/ELECTROSPRAY IONIZATION-MASS SPECTROMETRY

(71) Applicant: The University of Kansas, Lawrence, KS (US)

(72) Inventors: Craig E. Lunte, Lawrence, KS (US); Ryan Tyler Johnson, Lawrence, KS (US); Nhan To, Lawrence, KS (US); Susan M. Lunte, Lawrence, KS (US); Damon Osbourn, St. Louis, MO (US)

(73) Assignee: National Institutes of Health (NIH) U.S. Department of Health and Human Services (DHHS), U.S. Government NIH Division of Extramural Inventions and Technology Resources (DEITR), Bethesda, MD (US)

( * ) Notice: Subject to any disclaimer, the term of this patent is extended or adjusted under 35 U.S.C. 154(b) by 0 days.

(21) Appl. No.: 15/832,016

(22) Filed: Dec. 5, 2017

(65) Prior Publication Data
US 2018/0158663 A1    Jun. 7, 2018

Related U.S. Application Data

(60) Provisional application No. 62/430,079, filed on Dec. 5, 2016.

(51) Int. Cl.
| | | |
|---|---|---|
| *H01J 49/16* | (2006.01) | |
| *G01N 27/447* | (2006.01) | |
| *H01J 49/04* | (2006.01) | |
| *G01N 30/72* | (2006.01) | |

(52) U.S. Cl.
CPC ...... *H01J 49/167* (2013.01); *G01N 27/44713* (2013.01); *G01N 30/7233* (2013.01); *H01J 49/0431* (2013.01)

(58) Field of Classification Search
USPC ....................................................... 250/288
See application file for complete search history.

(56) References Cited

U.S. PATENT DOCUMENTS

| | | | | |
|---|---|---|---|---|
| 6,375,871 B1* | 4/2002 | Bentsen | ............ | B01L 3/502707 156/242 |
| 6,635,226 B1* | 10/2003 | Tso | ........................ | B01L 3/5027 422/129 |
| 2004/0075050 A1* | 4/2004 | Rossier | ................... | H01J 49/04 250/288 |

* cited by examiner

*Primary Examiner* — Kiet T Nguyen
(74) *Attorney, Agent, or Firm* — Meunier Carlin & Curfman LLC (57) ABSTRACT

Provided herein are capillaries for use in an electrophoretic separations. The capillaries can comprise an elongated tubular wall defining a path for fluid flow from an inlet to a tapered outlet; and a decoupler junction positioned within the elongated tubular wall upstream of the tapered outlet. The decoupler junction can comprise a plurality of microchannels penetrating through the elongated tubular wall and an ion-permeable polymer coating the plurality of microchannels. Also provided are sheathless interfaces for coupling capillary electrophoresis (CE) with mass spectrometry that employ these capillaries.

20 Claims, 5 Drawing Sheets

SHEATHLESS INTERFACE FOR CAPILLARY ELECTROPHORESIS/ELECTROSPRAY IONIZATION-MASS SPECTROMETRY

CROSS REFERENCE TO RELATED APPLICATIONS

This application claims benefit of U.S. Provisional Patent Application No. 62/430,079, filed Dec. 5, 2016, which is hereby incorporated herein by reference in its entirety.

STATEMENT REGARDING FEDERALLY SPONSORED RESEARCH OR DEVELOPMENT

This invention was made with Government Support under Grant No. R01 NS066466 awarded by the National Institutes of Health. The Government has certain rights in the invention.

BACKGROUND

The coupling of capillary electrophoresis (CE) with electrospray-mass spectrometry (ESI-MS) has shown great utility in the analysis of biological matrices. Attributes of CE include low sample and solvent consumption, potentially uncomplicated method development and high efficiency/peak capacity separations. When interfaced with MS, one gains an orthogonal second separation dimension, thus enhancing overall system peak capacity together with the gain of high selectivity and sensitivity via ESI-MS detection. Despite the many advantages of CE-ESI-MS, it has not been widely utilized in the bioanalytical field due to the expertise required to fabricate and operate the interface.

Two interfaces have been developed that enable CE-ESI-MS coupling: the sheath-flow interface and the sheathless interface. Sheath-flow interfaces establish the CE circuit by supplying a flowing conductive 'sheath' solution to the capillary outlet enclosed within a stainless steel needle. Application of an appropriate potential to the needle results in the generation of an electrospray from mixing the sheath and the CE effluent. The sheath-flow interface features robust electrospray and easy implementation, but suffers from an inherent loss of analyte sensitivity due to dilution.

To overcome this shortcoming, sheathless interfaces have been developed. When interfacing with ESI-MS, the terminal electrical connection of the CE is held at an ESI potential. Sheathless interfaces have been fabricated that employ electrode insertion or metal deposition at the capillary terminus, a microdialysis junction, a small hand-drilled crack, or hydrofluoric etching to introduce a terminus voltage. While these designs can improve sensitivity relative to sheath-flow interfaces, they can suffer from short capillary lifetimes, dead volume, irreproducible fabrication, fragility, or requiring expertise in handling hydrofluoric acid.

Accordingly, improved devices, systems, and methods for interfacing CE with ESI-MS are needed.

SUMMARY

Provided herein are capillaries for use in an electrophoretic separations. The capillaries can comprise an elongated tubular wall defining a path for fluid flow (i.e., a lumen) from an inlet to a tapered outlet; and a decoupler junction positioned within the elongated tubular wall upstream of the tapered outlet. The decoupler junction can comprise a plurality of microchannels penetrating through the elongated tubular wall and an ion-permeable polymer coating the plurality of microchannels.

The positioning of the decoupler junction upstream of the tapered outlet can vary. For example, in some embodiments, the decoupler junction can be positioned from 0.1 cm to 10 cm (e.g., from 2 cm to 10 cm, or from 2 cm to 10 cm) upstream of the tapered outlet.

The decoupler junction can comprise any suitable number of microchannels. For example, in some embodiments, the decoupler junction can comprise 5 or more microchannels (e.g., from 5 to 30 microchannels, from 15 to 30 microchannels, or from 5 to 20 microchannels). Each of the plurality of microchannels can be spaced apart by a distance of less than 250 microns (e.g., a distance of less than 100 microns, such as a distance of from 10 microns to 100 microns, from 10 microns to 50 microns, or 15 microns to 40 microns). In some cases, the plurality of microchannels can be equally spaced apart. For example, in some embodiments, the plurality of microchannels can comprise at least three microchannels, and each of the plurality of microchannels can be spaced apart by substantially equal distances (e.g., each of the plurality of microchannels can be spaced apart by a distance of ±10 microns, ±5 microns, or ±2.5 microns).

The orientation of the plurality of microchannels within the decoupler junction can vary. In some embodiments, the plurality of microchannels can be axially spaced apart along the elongated tubular wall. In some embodiments, the plurality of microchannels can be aligned along the elongated tubular wall (e.g., aligned along an axis parallel to the long axis of the capillary running down the center of the lumen from the capillary inlet to the tapered capillary outlet). In certain embodiments, the plurality of microchannels can be axially spaced apart and aligned along the elongated tubular wall. This arrangement of microchannels can serve to preserve the mechanical durability of the capillary.

The dimensions of the microchannels can be varied. The microchannels can have a characteristic cross-sectional dimension (e.g., a minimum cross-sectional dimension at the point where the microchannel joins the lumen of the capillary, as measured by microscopy) of from 1 micron to 50 microns (e.g., from 5 microns to 50 microns, or from 20 microns to 50 microns). In some cases, the plurality of microchannels can have substantially equal characteristic cross-sectional dimensions (e.g., each of the plurality of microchannels can have a characteristic cross-sectional dimension within ±10 microns, ±5 microns, or ±2.5 microns of each other).

The number of microchannels in the decoupler junction, as well as the dimensions of these microchannels, can be selected in order to provide decoupler having the desired surface area for a particular device design. In some embodiments, the plurality of microchannels provide a surface area of from $2500\ \mu m^2$ to $15000\ \mu m^2$ (e.g., a surface area of from $4000\ \mu m^2$ to $15000\ \mu m^2$, or a surface area of from $5000\ \mu m^2$ to $12000\ \mu m^2$).

The ion-permeable polymer can comprise any suitable ion-permeable polymer. In some cases, the ion-permeable polymer can comprise a non-ionic polymer. In some cases, the ion-permeable polymer can comprise a hydrophilic polymer. In some cases, the ion-permeable polymer can comprise an ion-exchange polymer. In certain embodiments, the ion-permeable polymer can comprise a non-ionic, hydrophilic polymer, such as cellulose acetate. In certain embodiments, the ion-permeable polymer can comprise an ion-exchange polymer, such as nafion. The ion-permeable polymer coating the plurality of microchannels can have a thickness of 350 microns or less (e.g., 200 microns or less, or 100 microns or less). In certain cases, the ion-permeable polymer coating the plurality of microchannels can have a thickness of from 25 microns to 100 microns.

Also provided herein are methods of forming capillaries for use in electrophoretic separations. These methods can include (a) providing an electrophoretic capillary comprising an elongated tubular wall defining a path for fluid flow from a capillary inlet to a capillary outlet; (b) modifying the capillary outlet to form a tapered outlet; (c) laser ablating a plurality of microchannels penetrating through the elongated tubular wall; and (d) coating the plurality of microchannels with an ion-permeable polymer.

In some examples, modifying the capillary outlet to form a tapered outlet can comprise sharpening the capillary outlet to form a tapered outlet. For example, the capillary outlet can be sharpened by mechanical means, such as physical abrasion or sanding of the elongated tubular wall to locally reduce the outer diameter of the capillary at the outlet. Modifying the capillary outlet to form a tapered outlet can also comprise, for example, etching the capillary outlet (e.g., using HF) to form a tapered outlet, or mechanically stretching the capillary outlet under applied heat. The microchannels can be laser ablated using any suitable laser, such as a carbon dioxide laser ($CO_2$ laser). Coating the plurality of microchannels with an ion-permeable polymer can comprise contacting the plurality of microchannels with an ion-permeable polymer (e.g., an ion-permeable polymer solution), and curing the ion-permeable polymer (e.g., by heating the capillary in an oven). Optionally, coating the plurality of microchannels with an ion-permeable polymer can further comprise treating the ion-permeable polymer to increase its ion permeability.

In some embodiments, a wire (e.g., a tungsten metal wire having a diameter slightly smaller than the inner diameter of the capillary) can be disposed within the electrophoretic capillary during step (b), step (c), step (d), or a combination thereof. The wire can serve to stabilize the capillary during fabrication. In addition, the wire can minimize damage to the capillary lumen during fabrication. Optionally, methods can further comprise conditioning the capillary (e.g., by rinsing the capillary with a basic solution), coating the capillary, or a combination thereof.

The capillaries described herein can be used to create efficient, durable, and reliable interfaces for coupling CE with ESI-MS. Accordingly, also provided are sheathless interfaces for coupling capillary electrophoresis (CE) with mass spectrometry. The interfaces can comprise a capillary described herein, a buffer reservoir in liquid contact with the decoupler junction of the capillary and filed with a reservoir liquid; and an electrode in contact with the reservoir liquid.

This system can further comprise a power supply electrically connected to the electrode. The power supply is configured to apply a potential across the capillary to perform an electrophoretic separation within the capillary. The electrophoretic separation can comprise, for example, capillary zone electrophoresis (CZE) separation, capillary isotachophoresis (CITP), capillary isoelectric Focusing (CIEF), or capillary electrochromatography.

The tapered outlet of the capillary can be directed towards the entrance of a mass spectrometer, such that analytes emitted from the tapered outlet of the capillary can be directed into a mass spectrometer for analysis. The mass spectrometer can comprise a quadrupole mass spectrometer, a time of flight mass spectrometer, an ion trap mass spectrometer, a Fourier transform ion cyclotron resonance mass spectrometer, an Orbitrap mass spectrometer, or a combination thereof.

Also provided herein are methods of characterizing a sample comprising one more analytes. These methods can comprise, for example, providing a sheathless interface for coupling capillary electrophoresis (CE) with mass spectrometry described herein; injecting the sample into the inlet of the capillary; electrophoretically separating the sample; and directing the separated sample into the entrance of the mass spectrometer. One or more analytes in the separated sample can then be detected by the mass spectrometer. The sheathless interface can comprise a capillary described herein; a buffer reservoir in liquid contact with the decoupler junction of the capillary and filed with a reservoir liquid; an electrode in contact with the reservoir liquid; a mass spectrometer comprising an entrance and a detector, wherein the tapered outlet of the capillary is directed towards the entrance of a mass spectrometer; and a power supply electrically connected to the electrode, wherein the power supply is configured to apply a potential across the capillary.

DETAILED DESCRIPTION

Figure 1A:
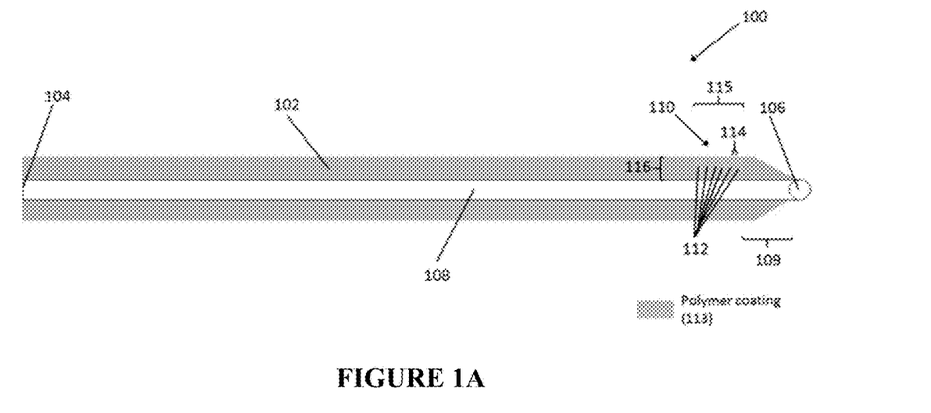
FIG. 1A is a schematic illustration of a capillary for use in an electrophoretic separation.

Disclosed herein are capillaries for use in an electrophoretic separations. Referring now to FIG. 1A, the capillaries (100) can comprise an elongated tubular wall (102) defining a path for fluid flow (i.e., a lumen, 108) that stretches from an inlet (104) to a tapered outlet (106). Though described and illustrated as having a tubular shape and containing a lumen with a circular cross-sectional shape, the capillaries described herein (as well as the interior lumen running within the capillaries) can have any desired shape (e.g., square, rectangular, diamond, triangular, ovoid, circular, etc.). The capillaries can further comprise a decoupler junction (110) positioned within the elongated tubular wall upstream of the tapered outlet (106). The decoupler junction can comprise a plurality of microchannels (112) penetrating through the elongated tubular wall and an ion-permeable polymer (112) coating the plurality of microchannels.

Figure 1B:
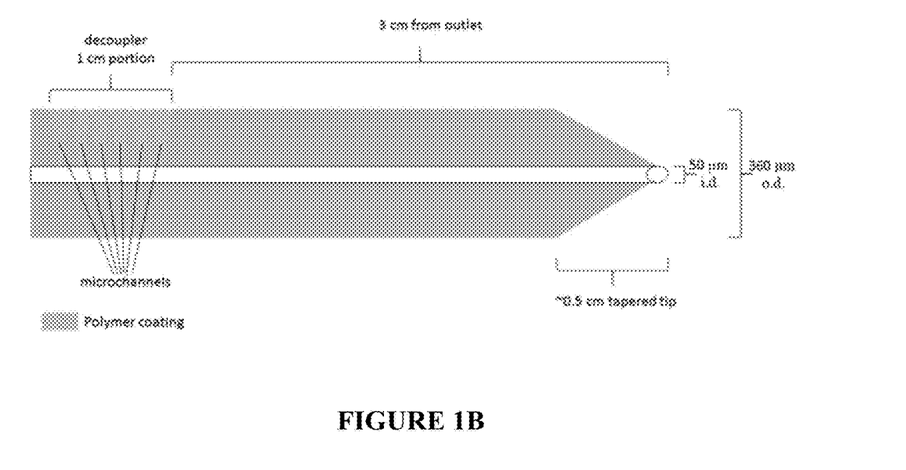
FIG. 1B is a schematic illustration of a region of the capillary of shown in FIG. 1A near the tapered outlet of the capillary. Certain example dimensions are illustrated.
Figure 1C:
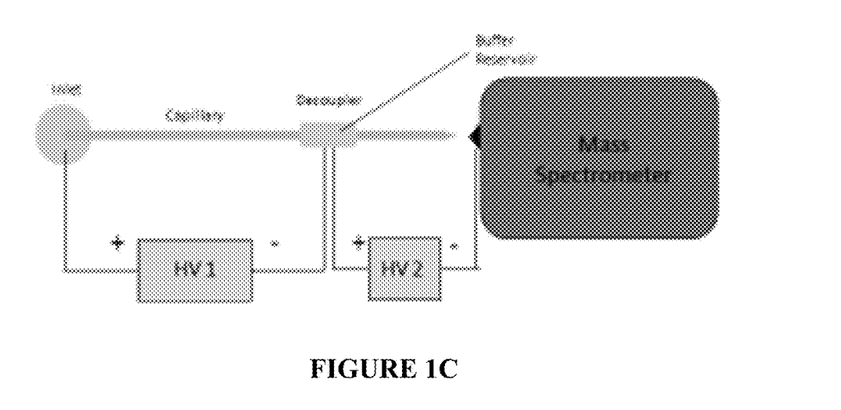
FIG. 1C is a schematic illustration of an example CE-ESI-MS system employing a sheathless interface described herein.

The positioning of the decoupler junction upstream of the tapered outlet can vary. For example, in some embodiments, the decoupler junction can be positioned a distance (109) of from 0.1 cm to 10 cm (e.g., from 2 cm to 10 cm, or from 2 cm to 10 cm) upstream of the tapered outlet (106). The size of the decoupler junction can also vary. In some examples, the decoupler junction can have a length (115), measured as the distance from the most upstream microchannel to the most downstream microchannel along the long axis of the capillary running down the center of the lumen from the capillary inlet to the tapered capillary outlet, of from 0.2 cm to 2 cm (e.g., from 0.5 cm to 1.5 cm).

The decoupler junction can comprise any suitable number of microchannels. For example, in some embodiments, the decoupler junction can comprise at least 3 microchannels (e.g., at least 4 microchannels, at least 5 microchannels, at least 10 microchannels, at least 15 microchannels, at least 20 microchannels, at least 25 microchannels, at least 30 microchannels, at least 35 microchannels, at least 40 microchannels, at least 45 microchannels, at least 50 microchannels, or more). In some embodiments, the decoupler junction can comprise 50 microchannels or less (e.g., 45 microchannels or less, 40 microchannels or less, 35 microchannels or less, 30 microchannels or less, 25 microchannels or less, 20 microchannels or less, 15 microchannels or less, 10 microchannels or less, or 5 microchannels or less).

The decoupler junction can comprise a number of microchannels ranging from any of the minimum values described above to any of the maximum values described above. For example, in some embodiments, the decoupler junction can comprise from 3 to 50 microchannels (e.g., from 5 to 50 microchannels, from 3 to 30 microchannels, from 5 to 30 microchannels, from 15 to 30 microchannels, or from 5 to 20 microchannels).

Each of the plurality of microchannels can be spaced apart by a distance (114) of less than 250 microns (e.g., a distance of less than 100 microns, such as a distance of from 10 microns to 100 microns, from 10 microns to 50 microns, or 15 microns to 40 microns). In some cases, the plurality of microchannels can be equally spaced apart. For example, in some embodiments, the plurality of microchannels can comprise at least three microchannels, and each of the plurality of microchannels can be spaced apart by substantially equal distances (e.g., each of the plurality of microchannels can be spaced apart by a distance of ±10 microns, ±5 microns, or ±2.5 microns).

The orientation of the plurality of microchannels within the decoupler junction can vary. In some embodiments, the plurality of microchannels can be axially spaced apart along the elongated tubular wall. In some embodiments, the plurality of microchannels can be aligned along the elongated tubular wall (e.g., aligned along an axis parallel to the long axis of the capillary running down the center of the lumen from the capillary inlet to the tapered capillary outlet). In certain embodiments, the plurality of microchannels can be axially spaced apart and aligned along the elongated tubular wall. This arrangement of microchannels can serve to preserve the mechanical durability of the capillary.

The dimensions of the microchannels can be varied. The microchannels can have a characteristic cross-sectional dimension (e.g., a minimum cross-sectional dimension at the point where the microchannel joins the lumen of the capillary, as measured by microscopy) of from 1 micron to 50 microns (e.g., from 5 microns to 50 microns, from 20 microns to 50 microns). The microchannels can also have a characteristic cross-sectional dimension (e.g., a minimum cross-sectional dimension at the point where the microchannel joins the lumen of the capillary, as measured by microscopy) of less than 1 micron (e.g., from 250 nm to micron, or from 500 nm to 1 micron). In some cases, the plurality of microchannels can have substantially equal characteristic cross-sectional dimensions (e.g., each of the plurality of microchannels can have a characteristic cross-sectional dimension within ±10 microns, ±5 microns, or ±2.5 microns of each other).

The number of microchannels in the decoupler junction, as well as the dimensions of these microchannels, can be selected in order to provide decoupler having the desired surface area for a particular device design. In some embodiments, the plurality of microchannels provide a surface area of from 2500 $\mu m^2$ to 15000 $\mu m^2$ (e.g., a surface area of from 4000 $\mu m^2$ to 15000 $\mu m^2$, or a surface area of from 5000 $\mu m^2$ to 12000 $\mu m^2$).

The ion-permeable polymer can comprise any suitable ion-permeable polymer. In some cases, the ion-permeable polymer can comprise a non-ionic polymer. In some cases, the ion-permeable polymer can comprise a hydrophilic polymer. In certain embodiments, the ion-permeable polymer can comprise a non-ionic, hydrophilic polymer, such as cellulose acetate. In other embodiments, the ion-permeable polymer can comprise an ionic polymer (e.g., an ionomer). For example, the ionic polymer can comprise an ion-exchange polymer, such as nafion (a sulfonated tetrafluoroethylene-based fluoropolymer-copolymer). The ion-permeable polymer coating the plurality of microchannels can have a thickness (116) of 350 microns or less (e.g., 200 microns or less, or 100 microns or less). In certain cases, the ion-permeable polymer coating the plurality of microchannels can have a thickness of from 25 microns to 100 microns.

While described herein as a capillary, it is understood the capillaries described herein can be of any suitable length. Accordingly, in some embodiments, the capillaries can have an extended length, such as from 15 cm to 100 cm in length. In these embodiments, the capillary can be used as a separation capillary, for example, in capillary electrophoresis. In other embodiments, the capillary can have a much shorter length, such as a length of 15 cm or less (e.g., from 15 cm to 1 cm, from 15 cm to 2 cm, from 15 cm to 5 cm, from 10 cm to 1 cm, from 10 cm to 2 cm, or from 15 cm to 5 cm). In these embodiments, the capillary described herein can be a tip which can be interfaced with a longer capillary (e.g., a separation capillary), as needed. In this way, the decoupler can be provided as part of a replaceable tip that can be detachably connected to any existing capillary as needed (e.g., in the event that the decoupler junction degrades).

In some of these embodiments, the tip can have a smaller outer diameter than the inner diameter of the separation capillary, such that the tip can be inserted into one end of the separation capillary. In other cases, the tip can have a same or similar inner and/or outer diameter as the separation capillary. In these embodiments, the tip can be connected to the separation catheter using standard methods known in the art (e.g., using an adhesive/epoxy of with a segment of tubing with a slightly larger inner diameter than the outer diameter of the separation capillary and tip).

Also provided herein are methods of forming capillaries for use in electrophoretic separations. These methods can include (a) providing an electrophoretic capillary comprising an elongated tubular wall defining a path for fluid flow from a capillary inlet to a capillary outlet; (b) modifying the capillary outlet to form a tapered outlet; (c) laser ablating a plurality of microchannels penetrating through the elongated tubular wall; and (d) coating the plurality of microchannels with an ion-permeable polymer.

In some examples, modifying the capillary outlet to form a tapered outlet can comprise sharpening the capillary outlet to form a tapered outlet. For example, the capillary outlet can be sharpened by mechanical means, such as physical abrasion or sanding of the elongated tubular wall to locally reduce the outer diameter of the capillary at the outlet. Modifying the capillary outlet to form a tapered outlet can also comprise, for example, chemically etching the capillary outlet (e.g., using HF) to form a tapered outlet, or mechanically stretching the capillary outlet under applied heat (also referred to as pulling the capillary). The microchannels can be laser ablated using any suitable laser, such as a carbon dioxide laser ($CO_2$ laser). Coating the plurality of microchannels with an ion-permeable polymer can comprise contacting the plurality of microchannels with an ion-permeable polymer (e.g., an ion-permeable polymer solution), and curing the ion-permeable polymer (e.g., by heating the capillary in an oven). Optionally, coating the plurality of microchannels with an ion-permeable polymer can further comprise treating the ion-permeable polymer to increase its ion permeability.

In some embodiments, a wire (e.g., a tungsten metal wire having a diameter slightly smaller than the inner diameter of the capillary) can be disposed within the electrophoretic capillary during step (b), step (c), step (d), or a combination thereof. The wire can serve to stabilize the capillary during fabrication. In addition, the wire can minimize damage to the capillary lumen during fabrication. Optionally, methods can further comprise conditioning the capillary (e.g., by rinsing the capillary with a basic solution), coating the capillary, or a combination thereof.

The capillaries described herein can be used to create efficient, durable, and reliable interfaces for coupling CE with ESI-MS. Accordingly, also provided are sheathless interfaces for coupling capillary electrophoresis (CE) with mass spectrometry. The interfaces can comprise a capillary described herein, a buffer reservoir in liquid contact with the decoupler junction of the capillary and filed with a reservoir liquid; and an electrode in contact with the reservoir liquid.

This system can further comprise a power supply electrically connected to the electrode. The power supply is configured to apply a potential across the capillary to perform an electrophoretic separation within the capillary. The electrophoretic separation can comprise, for example, capillary zone electrophoresis (CZE) separation, capillary isotachophoresis (CITP), capillary isoelectric focusing (CIEF), or capillary electrochromatography.

The tapered outlet of the capillary can be directed towards the entrance of a mass spectrometer, such that analytes emitted from the tapered outlet of the capillary can be directed into a mass spectrometer for analysis. The mass spectrometer can comprise, for example, a quadrupole mass spectrometer, a time of flight mass spectrometer, an ion trap mass spectrometer, a Fourier transform ion cyclotron resonance mass spectrometer, an Orbitrap mass spectrometer, or a combination thereof.

In some embodiments, the inlet of a capillary described herein can be fluidly connected to an outlet of a microfluidic device (e.g., a lab-on-a-chip system). A buffer reservoir can further be present in liquid contact with the decoupler junction of the capillary and filed with a reservoir liquid, along with an electrode in contact with the reservoir liquid.

The tapered outlet of the capillary can be directed towards the entrance of a mass spectrometer, such that analytes emitted from the tapered outlet of the capillary can be directed into a mass spectrometer for analysis. In some embodiments, a separation and/or reaction can be performed within the microfluidic device, and then the outflow from the microfluidic device can directed from the tapered outlet of the capillary can be directed into a mass spectrometer for analysis. In certain embodiments, outflow from the microfluidic device can directed into the capillary, an electrophoretic separation can be performed within the capillary, and then separated sample can directed from the tapered outlet of the capillary can be directed into a mass spectrometer for analysis.

Also provided herein are methods of characterizing a sample comprising one more analytes. These methods can comprise, for example, providing a sheathless interface for coupling capillary electrophoresis (CE) with mass spectrometry described herein; injecting the sample into the inlet of the capillary; electrophoretically separating the sample; and directing the separated sample into the entrance of the mass spectrometer. The sheathless interface can comprise a capillary described herein; a buffer reservoir in liquid contact with the decoupler junction of the capillary and filed with a reservoir liquid; an electrode in contact with the reservoir liquid; a mass spectrometer comprising an entrance and a detector, wherein the tapered outlet of the capillary is directed towards the entrance of a mass spectrometer; and a power supply electrically connected to the electrode, wherein the power supply is configured to apply a potential across the capillary. By way of non-limiting illustration, examples of certain embodiments of the present disclosure are given below.

EXAMPLES

Example 1: Sheathless Interface for Capillary Electrophoresis Electrospray Ionization Mass Spectrometry Using a Cellulose Acetate Cast Capillary In this example, the design and fabrication of a robust sheathless CE-ESI-MS interface is described. The interface employs a cellulose acetate decoupler. A programmable $CO_2$ laser was used to ablate small channels in the walls of a polyimide capillary near the terminus. Subsequent exposure of the channel region to a cellulose acetate solution followed by drying resulted in the formation of an electrically conductive semi-permeable membrane. The decoupler was then immersed in a conductive buffer reservoir. Application of an appropriate voltage to the reservoir simultaneously established the electrical connection for both CE and ESI. The use of the conductive buffer reservoir to complete the CE and ESI circuits also allows for pH perturbation of post CE separation zones for enhancement of ionization efficiency, thus improving detection sensitivity. Fabrication details, operational aspects and preliminary results are also described below.

Methods and Materials

Chemicals

Angiotensin II, Val-Tyr-Val, Leu-enkephalin, Met-enkephalin, cellulose acetate, ammonium acetate, and glacial acetic acid were purchased from Sigma-Aldrich (St. Louis, Mo., USA). Acetone (HPLC grade), water (MS grade) and ammonium hydroxide stock were purchased from Fisher Scientific (Waltham, Mass., USA). Peptide stock solutions were prepared in MS grade water and diluted into 30 mM ammonium acetate background electrolyte (BGE). Cellulose acetate solution was prepared as 6% weight/volume (w/v) in acetone. Buffers were prepared from solid ammonium acetate and adjusted to the appropriate pH using aqueous 1 M acetic acid or ammonium hydroxide.

Instrumentation and Apparatus

CE-UV:

The separation of peptide standards was optimized using a P/ACE MDQ Capillary Electrophoresis System equipped with a diode array detector (Beckman Coulter, Palo Alto, Calif., USA). A 65 cm length×50 µm i.d.×360 µm o.d. capillary (Polymicro Technologies, Tucson, Ariz., USA) with a 55 cm effective length was used for all CE-UV studies. Prior to injection, CE capillaries were sequentially conditioned at 10 psi for 5 minutes each with nanopure water, 0.1 M ammonium hydroxide, and BGE. For all the sample injections, hydrodynamic injection of 5 psi for 2 seconds was performed.

Figure 2:
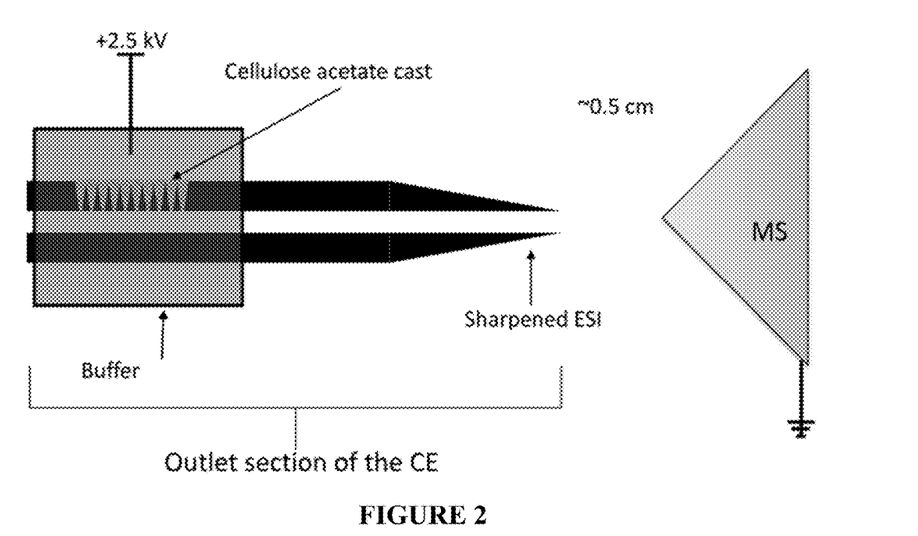
FIG. 2 is a schematic of an example cellulose acetate cast CE-ESI-MS interface.

Interface Fabrication:

The schematic in FIG. 2 shows the electrical configuration and design of the interface. The capillary tip was sharpened using a Dremel (6500 rpm, Mt. Prospect, Ill., USA) equipped with 600 grit wet sanding paper. A 46 µm tungsten wire from California Fine Wire (Grover Beach, Calif., USA) was threaded 10 cm into the outlet of a 55 cm length capillary. The capillary inlet was secured to a second Dremel to provide constant rotation of the capillary. The capillary outlet was placed against the sanding disc at a 20° angle for 5 min and then inspected under microscope to ensure tip uniformity.

Figure 3A:
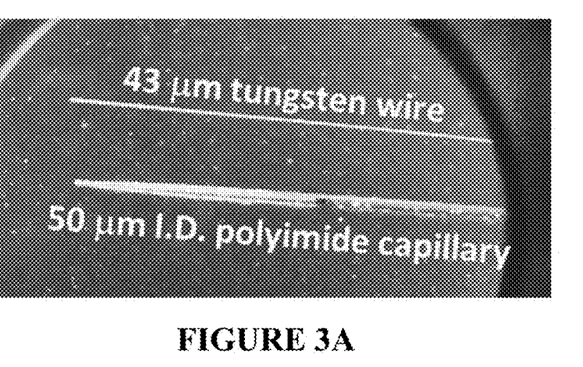
FIGS. 3A-3C illustrate steps involved in fabricating a capillary for use in an electrophoretic separation that includes a cellulose acetate decoupler junction.
Figure 3B:
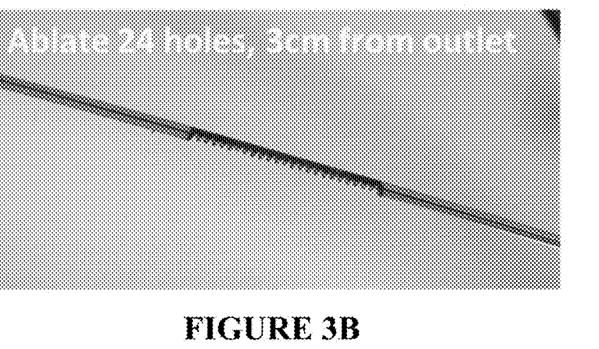
Figure 3C:
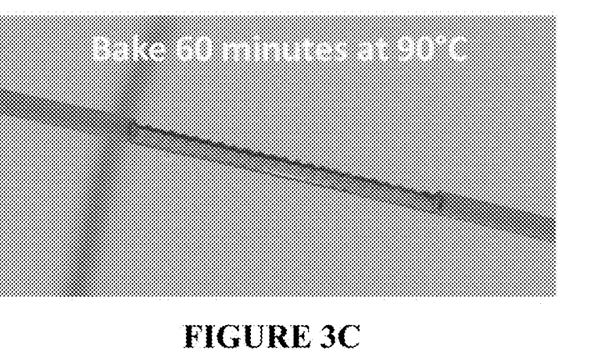

Without removing the tungsten wire from the capillary outlet, a $CO_2$ laser (Boss Laser, Sanford, Fla., USA) set to 30% power, 20 mm/s speed, with six replicate ablations was used to introduce 24 channels perpendicular to the capillary length. The channels were made 5 cm from the capillary outlet spanning a 1 cm section. The tungsten wire was displaced 1 cm to provide a smooth surface for coating. Using a 20 G syringe, cellulose acetate dissolved in acetone (6% w/v) was used to coat the ablated portion of the capillary. The coated capillary was baked at 90° C. for one hour and tweezers were used to remove the tungsten wire from the capillary outlet. The coated capillary was sequentially rinsed with nanopure water and 0.1 M ammonium hydroxide at 10 psi for 1 h for conditioning. FIG. 3A-3C illustrate the interface at various points during the fabrication process.

Figure 4:
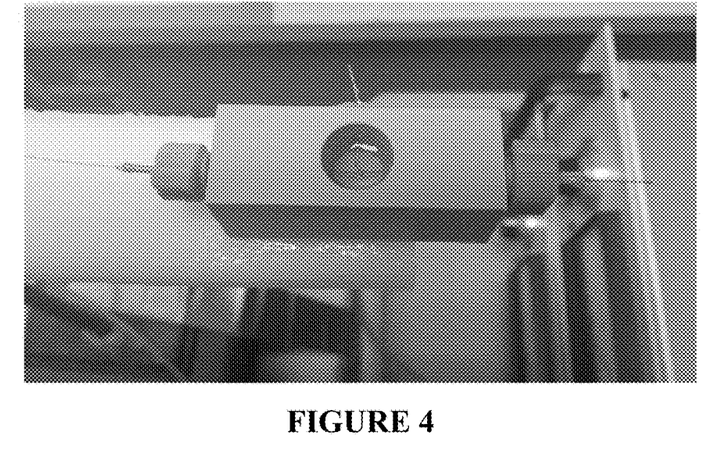
FIG. 4 illustrates the cellulose acetate decoupler immersed in a conductive buffer reservoir.

The modified capillary was inserted into a machined PEEK housing attached to an XYZ positioner and secured using PEEK fittings as shown in FIG. 4. The PEEK housing contained a buffer reservoir with a platinum electrode for the application of the terminus voltage. Two CZE1000R Spellman high voltage power supplies (Hauppauge, N.Y., USA) were used to apply CE and ESI potentials. The CE and ESI power supplies were operated in positive voltage mode. The schematic in FIG. 2 shows the electrical configuration and design of the interface. All CE-MS experiments were conducted using a LTQ-XL MS from Thermo Scientific (Waltham, Mass., USA). Detection was performed in positive ion mode using single reaction monitoring of Val-Tyr-Val (m/z 380.5->263), Leu-enkephalin (m/z 556.5->425), Met-enkephalin (m/z 574.5->425), and angiotensin II (m/z 1047->932) at an 'enhanced' scan rate.

Results and Discussion

Interface Design

Past efforts in the development of CE-ESI-MS interfaces have been based on sheath-flow and sheathless approaches. In this example, efforts have focused on the development of an interface that does not compromise sensitivity. As part of this effort, a reproducible fabrication procedure has also been developed that produces an operationally robust interface. In order to improve sensitivity, a sheathless interface design was designed. The design of the interface includes a beveled tip at the terminus of the capillary and a conductive region proximal to the terminus of the capillary. The conductive region includes a polymeric coating covering the conductive region. Functionally, the beveled terminus facilitates an efficient ESI spray, the conductive region allows the electrical connections for CE and ESI to be established simultaneously, and encircling the conductive region with a polymeric coating prevents dilution, provides structural integrity, and allows the transport of small ions, providing the ability to modify pH in the post-CE region. These concepts and features are illustrated in FIG. 2.

Interface Fabrication

With the design details identified, a practical and reproducible procedure for interface fabrication was developed. Initially one selects the desired length of capillary (typically 55 cm length, 360 µm o.d, 50 µm i.d.) and inserts a tungsten wire into the capillary outlet, which serves to stabilize the capillary during fabrication operations. Using a Dremel Tool fitted with a sanding disk, rotating motion served to create the desired beveled terminal region (refer to the illustration of FIG. 2). With the tungsten wire still in place, the next step involved utilization of a programmable $CO_2$ laser to simultaneously create a series of ablations in each of a group of capillaries a short distance from the capillary terminus. In a final step, the ablated region was coated with a solution of cellulose acetate dissolved in acetone. Subsequent heating resulted in the formation of a membrane that provides structural support; however, cellulose membranes formed from casting of acetone solutions exhibit limited permeability to water vapor and may not provide for desirable transport properties, including permeability to various ions and protons that allow for the establishment of the electrical circuit and pH perturbation of the CE running buffer. Consequently, after removal of the tungsten wire, the entire capillary was rinsed with a strongly basic solution for approximately one hour in order to increase the cast membrane permeability.

Perspectives and Operational Aspects

Fused-silica capillary electrospray can be fabricated using flame pulling, etching with hydrofluoric acid, and mechanical sharpening. For the cellulose acetate cast capillaries, mechanical sharpening was chosen because the resulting capillary tips were not as susceptible to clogging as pulled tips and did not require the use of hydrofluoric acid. A tungsten wire was initially inserted at the capillary outlet during the sharpening process to prevent debris produced during the ablation process from getting lodged inside the capillary. The tungsten wire serves two additional purposes with respect to the fabrication of the cellulose acetate cast. First, during the ablation process, the wire ensures the laser pierces only one side of the capillary wall. The opposing side of the capillary diameter is protected from the laser and remains intact. Second, the tungsten wire prevents cellulose acetate from leaking into the ablated holes, which could result in clogging or coating of the silanol walls. The cellulose acetate does not bind to the tungsten, which allows it to be removed without damage to the inner diameter upon drying.

The cellulose acetate cast capillary for sheathless CE-ESI-MS has several advantages over existing designs. The absence of a metal tip allows the interface to be situated less than 0.5 cm from the MS inlet without arcing and bubble forming redox reactions. Using this design, the modified capillaries produced stable spray and were only replaced in rare cases of clogging. The cellulose acetate cast capillary is also mechanically stable, which can be attributed to the remaining polyimide opposite the laser ablations and refortification with cellulose acetate polymer. Securing the capillary into the interface housing further fortifies the interface. Nafion casts can also be used instead of cellulose acetate if additional structural support is desired, but may result in loss of cationic analytes. Lastly, the fabrication of the laser-ablated capillaries can be automated, allowing for high-throughput and reproducible capillary fabrication. Some solvents for non-aqueous CE (e.g., acetonitrile and acetone) may not be completely compatible with cellulose acetate cast capillaries, as leakage through the cellulose acetate polymer can occur. However, many solvents, including pure methanol, ethanol, and 2-propanol were tested and did not result in leakage through the membrane.

Capillary rinsing prior to CE-ESI-MS was conducted to prevent contamination of the MS and minimize inconsistencies in electroosmotic flow. Infusion of water for an hour, from the inlet to outlet direction, at 10 psi ensured that no particulates remained lodged within the capillary. Ammonium hydroxide (0.1 M) rinses were conducted prior to capillary use and between CE-ESI-MS runs to deprotonate the silanol walls and generate reproducible electroosmotic flow (EOF). Alternatively, a permanent charge can be generated on the capillary walls by coating the wall with a polymer containing negative charges. Such an approach typically requires chemical derivatization that may involve multiple steps, and if surface leaching occurs potentially represents an additional source of contamination to the MS. Utilizing the conditioning/reconditioning step with ammonium hydroxide results in an appropriate and consistent EOF.

Several parameters were tested to ensure that each capillary was capable of achieving reproducible migration times and stable spray. To ensure that the capillary was not clogged during the fabrication process, a plug of 10 µM Val-Tyr-Val was infused through the capillary and compared to the theoretical elution time for a 50 µm I.D.×55 cm length capillary at 10 psi (calculation per standard mobility equations). The elution time of the plug was consistent with that of an unmodified capillary (i.e., a capillary had not been subjected to laser ablation and casting with cellulose acetate). Prior to utilizing each capillary in the CE-ESI-MS format, CE current stability was monitored with the capillary containing background electrolyte with current variation of only 0.4-0.6% being observed. In further evaluations, migration time reproducibility and signal precision of four replicate injections of 10 µM Val-Tyr-Val were used to evaluate the interface. The migration time relative standard deviation for these injections was 1.1% and the signal precision was 4.1% for a 10 psi 1 sec injection. Detection response linearity was evaluated over a concentration range from 100 nM-10 µM, with an $r^2$=0.998. Based on S/N 3, the estimated LOD of Val-Tyr-Val was 8 nM or 0.2 femtomole using the aforementioned injection conditions. This value is in agreement with other CE-ESI-MS interfaces for peptide standards. Lastly, the spray stability at acidic and basic pH and with the assistance of pressure did not compromise the electrospray process. These observations demonstrate that the interface is suitable for routine CE-ESI-MS analysis.

Comparison of the CE-ESI-MS Interface System to a Commercial CE-UV System

Figure 5A:
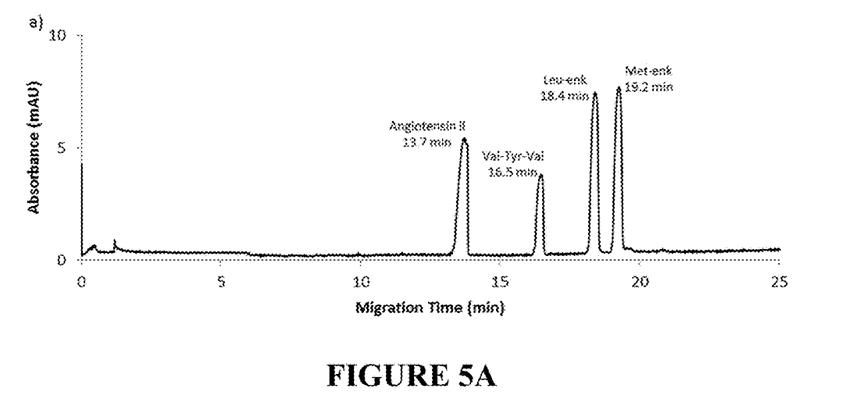
FIG. 5A shows the CE-UV separation of four peptide standards with commercial instrumentation.
Figure 5B:
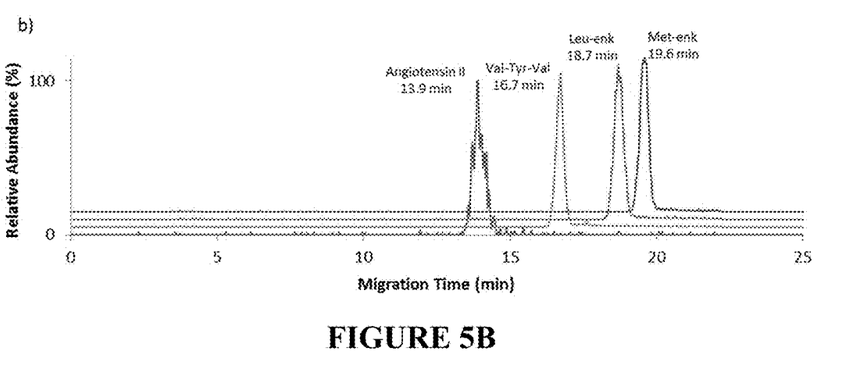
FIG. 5B shows the CE-ESI-MS separation of the same peptide standards with an in-house fabricated CE-System using the laser ablated cellulose acetate interface described herein.

To demonstrate that the CE separation does not degrade in the cellulose acetate cast capillary, CE-UV and CE-ESI-MS electropherograms for a peptide mixture containing angiotensin II, Val-Tyr-Val, Leu-enkephalin, and Met-enkephalin were obtained. The background electrolyte used for both analyses was 30 mM ammonium acetate adjusted to pH 2.8. Peptide standards of 50 µM and 1 µM were injected into the CE-UV and CE-ESI-MS systems, respectively. As shown in FIGS. 5A and 5B, baseline separation of the peptides was achieved with either method and migration times were comparable. A relative increase of 0.25 min peak widths was observed for CE-ESI-MS results. This was attributed to Joule heating, which is prevented with the thermostatically controlled Beckman CE-UV system. As opposed to several other CE-ESI-MS methods to establish spray at low pH, our method did not require pressure assistance or permanent capillary wall coating to create electrospray at low EOF strengths. These results demonstrate that with this interface, analytical separations are not compromised when compared to those from an unmodified capillary.

Post-Junction pH Modification

Figure 6:
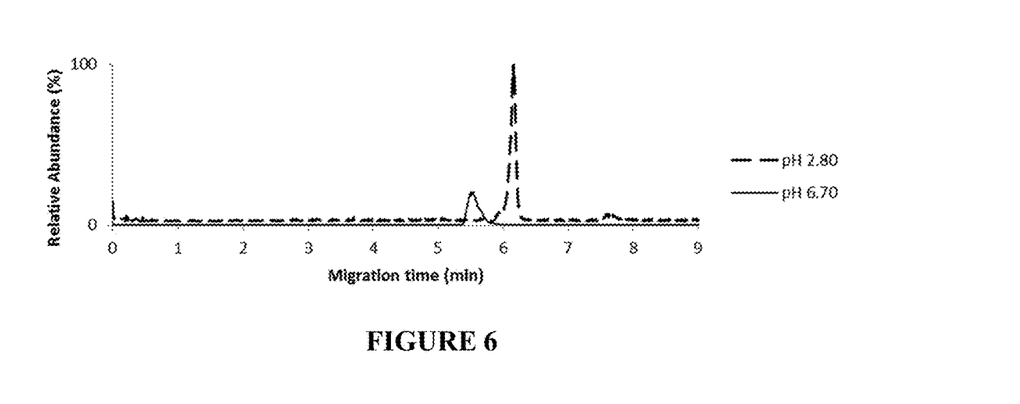
FIG. 6 shows a CE-ESI-MS spectra of Val-Tyr-Val conducted using 10 mM ammonium acetate at pH 6.7 BGE. The solid line is the electropherogram obtained when the buffer reservoir contains 10 mM ammonium acetate at pH 6.7 as BGE, while the dotted line shows an overlay of electropherograms obtained when the buffer reservoir contained 100 mM ammonium acetate at pH 2.8.

To achieve enhanced ionization efficiency, post-separation pH modification of the electrophoresis BGE buffer was evaluated using an acidic solution in the interface reservoir. This feature is desirable if the pH of the electrophoresis buffer does not provide optimal response or if the compound is to be separated as one charge and detected as another. For peptide Val-Tyr-Val with electrophoresis being conducted in 10 mM ammonium acetate of pH 6.7, comparisons were made with differing solutions in the interface reservoir. The first experimental condition utilized a pH 6.7 solution of 10 mM ammonium acetate, while in the next experiment a pH 2.8, 100 mM ammonium acetate buffer system was employed. With the more acidic buffer, an approximately 3.30-fold signal enhancement in the signal intensity was observed (n=3). The migration time using the acidic buffer was 0.5 min longer due to the decreased electroosmotic flow near the outlet (FIG. 6). The time required for the equilibration of pH between the reservoir and the capillary is dependent on the concentration and buffer capacity of the electrophoresis buffer. In these examples, equilibration was near instant because the chosen pH 6.7 BGE has limited buffer capacity. However, up to 8 hours may be required to achieve full titration of a BGE in its buffering range.

CONCLUSIONS

In this example, a novel CE-ESI-MS sheathless interface utilizing a cellulose acetate cast membrane has been described, which possesses several advantages over existing designs. The fabrication methodology allows several capillaries to be manufactured simultaneously in a procedure that avoids the tedious procedures and/or the highly caustic acids of previous designs. The use of a programmable laser omits the need for hand tools, resulting in reproducible ablations. The design is very mechanically stable upon coating with cellulose acetate and does not require difficult alignment steps that two-piece sheathless interfaces present. The interface produces a stable electrospray with lifetimes similar to that of unmodified fused silica capillaries. Additionally, this design does not inherently present a significant dead volume and due to the semi-permeable membrane, permits pH modification without introducing sample dilution.

The devices, systems, and methods of the appended claims are not limited in scope by the specific devices, systems, and methods described herein, which are intended as illustrations of a few aspects of the claims. Any devices, systems, and methods that are functionally equivalent are intended to fall within the scope of the claims. Various modifications of the devices, systems, and methods in addition to those shown and described herein are intended to fall within the scope of the appended claims. Further, while only certain representative devices, systems, and method steps disclosed herein are specifically described, other combinations of the devices, systems, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A capillary for use in an electrophoretic separation, the capillary comprising:
   (a) an elongated tubular wall defining a path for fluid flow from an inlet to a tapered outlet; and
   (b) a decoupler junction positioned within the elongated tubular wall upstream of the tapered outlet;
   wherein decoupler junction comprises a plurality of microchannels penetrating through the elongated tubular wall and an ion-permeable polymer coating the plurality of microchannels.

2. The capillary of claim 1, wherein the ion-permeable polymer comprises a non-ionic polymer.

3. The capillary of claim 1, wherein the ion-permeable polymer comprises a hydrophilic polymer.

4. The capillary of claim 1, wherein the ion-permeable polymer comprises an ion-exchange polymer.

5. The capillary of claim 1, wherein the ion-permeable polymer comprises cellulose acetate, nafion, or a combination thereof.

6. The capillary of claim 1, wherein the ion-permeable polymer coating the plurality of microchannels has a thickness of 100 microns or less.

7. The capillary of claim 6, wherein the ion-permeable polymer coating the plurality of microchannels has a thickness of from 25 microns to 100 microns.

8. The capillary of claim 1, wherein the plurality of microchannels comprises 5 or more microchannels.

9. The capillary of claim 8, wherein the plurality of microchannels comprises from 5 to 30 microchannels.

10. The capillary of claim 1, wherein each of the plurality of microchannels are spaced apart by a distance of from 10 microns to 50 microns.

11. The capillary of claim 1, wherein the plurality of microchannels comprises at least three microchannels, and wherein each of the plurality of microchannels are spaced apart by substantially equal distances.

12. The capillary of claim 1, wherein the plurality of microchannels provide a surface area of from 2500 $\mu m^2$ to 15000 $\mu m^2$.

13. The capillary of claim 1, wherein the plurality of microchannels are axially spaced apart along the elongated tubular wall.

14. The capillary of claim 1, wherein the plurality of microchannels are aligned along the elongated tubular wall.

15. The capillary of claim 1, wherein each of the plurality of microchannels has a characteristic cross-sectional dimension of from 5 microns to 50 microns.

16. The capillary of claim 1, wherein the decoupler junction is positioned from 0.1 cm to 10 cm upstream of the tapered outlet.

17. A sheathless interface for coupling capillary electrophoresis (CE) with mass spectrometry, the interface comprising:
   (a) the capillary of claim 1;
   (b) a buffer reservoir in liquid contact with the decoupler junction of the capillary and filed with a reservoir liquid; and
   (c) an electrode in contact with the reservoir liquid.

18. A method of characterizing a sample, the method comprising:
   (a) providing a sheathless interface for coupling capillary electrophoresis (CE) with mass spectrometry, the interface comprising:
      (i) the capillary of claim 1;
      (ii) a buffer reservoir in liquid contact with the decoupler junction of the capillary and filed with a reservoir liquid;
      (iii) an electrode in contact with the reservoir liquid;
      (iv) a mass spectrometer comprising an entrance and a detector, wherein the tapered outlet of the capillary is directed towards the entrance of a mass spectrometer; and
      (v) a power supply electrically connected to the electrode, wherein the power supply is configured to apply a potential across the capillary;
   (b) injecting the sample into the inlet of the capillary;
   (c) electrophoretically separating the sample;
   (d) directing the separated sample into the entrance of the mass spectrometer.

19. A method of forming a capillary for use in an electrophoretic separation, the method comprising:
   (a) providing an electrophoretic capillary comprising an elongated tubular wall defining a path for fluid flow from a capillary inlet to a capillary outlet;
   (b) modifying the capillary outlet to form a tapered outlet;
   (c) laser ablating a plurality of microchannels penetrating through the elongated tubular wall; and
   (d) coating the plurality of microchannels with an ion-permeable polymer.

20. The method of claim 19, wherein modifying the capillary outlet comprises sharpening the capillary outlet to form the tapered outlet.

* * * * *